(12) United States Patent
Ahlfors et al.

(10) Patent No.: US 7,416,896 B1
(45) Date of Patent: Aug. 26, 2008

(54) DETERMINATION OF PLASMA TOTAL AND UNBOUND BILIRUBIN USING ZONE FLUIDICS

(75) Inventors: Charles E. Ahlfors, Vashon, WA (US); Graham D. Marshall, Fox Island, WA (US); Duane K. Wolcott, Fox Island, WA (US)

(73) Assignees: Global FIA, Inc., Fox Island, WA (US); LW Ligang LLC, Miami, FL (US)

( * ) Notice: Subject to any disclaimer, the term of this patent is extended or adjusted under 35 U.S.C. 154(b) by 850 days.

(21) Appl. No.: 10/905,178

(22) Filed: Dec. 20, 2004

(51) Int. Cl.
*G01N 33/72* (2006.01)
(52) U.S. Cl. .............................. 436/97; 436/63; 436/174; 436/180; 422/68.1; 422/81; 422/82; 422/103
(58) Field of Classification Search .................. 436/12, 436/63, 97, 164, 166, 174, 180; 422/68.1, 422/81, 82, 82.05, 100, 103
See application file for complete search history.

(56) References Cited

U.S. PATENT DOCUMENTS

| | | | | | |
|---|---|---|---|---|---|
| 4,338,095 | A | * | 7/1982 | Wu | ............................ 436/97 |
| 4,412,005 | A | * | 10/1983 | Wu | ............................ 436/97 |
| 5,104,794 | A | * | 4/1992 | Kondo et al. | .................. 435/25 |
| 6,613,579 | B2 | * | 9/2003 | Wolcott | ...................... 436/178 |
| 6,887,429 | B1 | * | 5/2005 | Marshall et al. | ............... 422/81 |

OTHER PUBLICATIONS

Ahlfors et al. Clinica Chimica Acta, vol. 365, Oct. 5, 2005, pp. 78-85.*

* cited by examiner

*Primary Examiner*—Maureen M Wallenhorst
(74) *Attorney, Agent, or Firm*—Reginald F. Roberts, Jr.

(57) ABSTRACT

A method for determining total and bound plasma bilirubin. The method utilizes zone fluidics to enable accurate determination of the bilirubin using small volumes of sample and reagents, and significantly reduces dilution errors caused by inherent changes in bilirubin-binding with sample dilution, as well as the effects of weak bilirubin-binding competitors.

12 Claims, 1 Drawing Sheet

DETERMINATION OF PLASMA TOTAL AND UNBOUND BILIRUBIN USING ZONE FLUIDICS

BACKGROUND OF INVENTION

The present invention relates to instrumental chemical analysis. More particularly, the invention relates to the instrumental determination of bilirubin.

Plasma unbound or "free" bilirubin ($B_f$) is the fraction of bilirubin not bound to plasma albumin. $B_f$ is thought to be the bilirubin species most closely correlated with the risk of bilirubin toxicity in jaundiced newborns. Although newborn jaundice (hyperbilirubinemia) is usually a transient, benign event in the first week of life, in rare cases the accumulated unconjugated bilirubin causes irreversible brain damage or even death; see; for example, *Pediatrics,* 111, 1110 (2003). Technical difficulties and conflicting reports in the medical literature have limited the routine use of $B_f$ measurements to assess newborn jaundice. Instead, the readily available plasma total bilirubin concentration (TBC) is used, a measure that has repeatedly been shown to be inferior to $B_f$ as an indicator of bilirubin toxicity; see, e.g., *Pediatrics,* 93, 50 (1994); *Acta Paediatr. Jpn,* 34, 642 (1992); *Pediatrics,* 107, 665 (2001); *J. Pediatr,* 737, 540 (2000).

Only one FDA approved commercial device (UB-1 Analyzer, Arrows, LTD, Osaka, Japan) using the peroxidase test is available for measuring $B_f$. See *Clin. Chem.,* 20, 783 (1974); *J. Med. Sci,* 28, 91 (1982). The accuracy of this test is limited by the need for sample dilution (forty-two fold) which may inherently alter bilirubin-albumin binding by as much as tenfold and attenuate the effects of weak bilirubin binding competitors, which may be important clinically. See *J. Biol. Chem.,* 276, 29953 (2001); *J. Pediatr.,* 739, 317 (2001). The Arrows test also uses only a single concentration of peroxidase, which may cause underestimation of $B_f$ when bilirubin dissociation from albumin is rate limiting during the test. See *J. Pediatr.,* 708, 295 (1985). A method for measuring $B_f$ at minimal sample dilution and additional peroxidase concentrations is therefore needed and highly desirable.

SUMMARY OF INVENTION

In general, the present invention in a first aspect provides a method for determining plasma total bilirubin using zone fluidics. The method comprises (a) disposing a sample of plasma in a first reservoir; (b) disposing a first reagent in a second reservoir; (c) disposing a second reagent in a third reservoir; (d) connecting the first, second, and third reservoirs to a selection valve; (e) using the selection valve to dispose a first air zone in a holding coil; (f) using the selection valve to dispose a liquid zone in the holding coil by withdrawing, under conditions of fluid flow, portions of the first and second reagents from the second and third reservoirs, respectively, and of the sample from the first reservoir, and mixing the portions of the first and second reagents and of the sample in the holding coil; (g) using the selection valve to dispose a second air zone in the holding coil, thereby disposing the liquid zone between the first and second air zones, and forming a zone stack comprising the first air zone, the liquid zone, and the second air zone; (h) passing the zone stack by a detector; and (i) using the detector to generate a signal indicative of concentration of total bilirubin in the sample.

In a second aspect the invention provides a method for determining plasma unbound bilirubin. The method comprises (a) disposing a sample of plasma in a first reservoir; (b) disposing a first reagent in a second reservoir; (c) disposing a second reagent in a third reservoir; (d) disposing a third reagent in a fourth reservoir; (e) connecting the first, second, third, and fourth reservoirs to a selection valve; (f) using the selection valve to dispose a first air zone in a holding coil; (g) using the selection valve to dispose a first liquid zone in the holding coil by withdrawing, under conditions of fluid flow, portions of the second reagent, the third reagent, and the sample from the third, fourth, and first reservoirs, respectively, and mixing the portions of the second reagent, the third reagent, and the sample in the holding coil; (h) using the selection valve to dispose a second air zone in the holding coil, thereby disposing the first liquid zone between the first and second air zones, and forming a first zone stack comprising the first air zone, the first liquid zone, and the second air zone; (i) passing the first zone stack to a detector; (j) stopping fluid flow when the first zone stack reaches the detector; (k) observing change of signal from the detector over a period of time; (l) using the selection valve to dispose a third air zone in the holding coil; (m) using the selection valve to dispose a second liquid zone in the holding coil by withdrawing, under conditions of fluid flow, portions of the second reagent, the third reagent, the first reagent, and the sample from the third, fourth, second, and first reservoirs, respectively, and mixing the portions of the second reagent, the third reagent, the first reagent, and the sample in the holding coil; (n) using the selection valve to dispose a fourth air zone in the holding coil, thereby disposing the third liquid zone between the third and fourth air zones, and forming a second zone stack comprising the third air zone, the second liquid zone, and the fourth air zone; (o) passing the second zone stack to the detector; (p) stopping fluid flow when the second zone stack reaches the detector; (q) observing change of signal from the detector over a period of time; and (r) calculating concentration of unbound bilirubin from rates of change of detector response.

DETAILED DESCRIPTION

Figure 1:
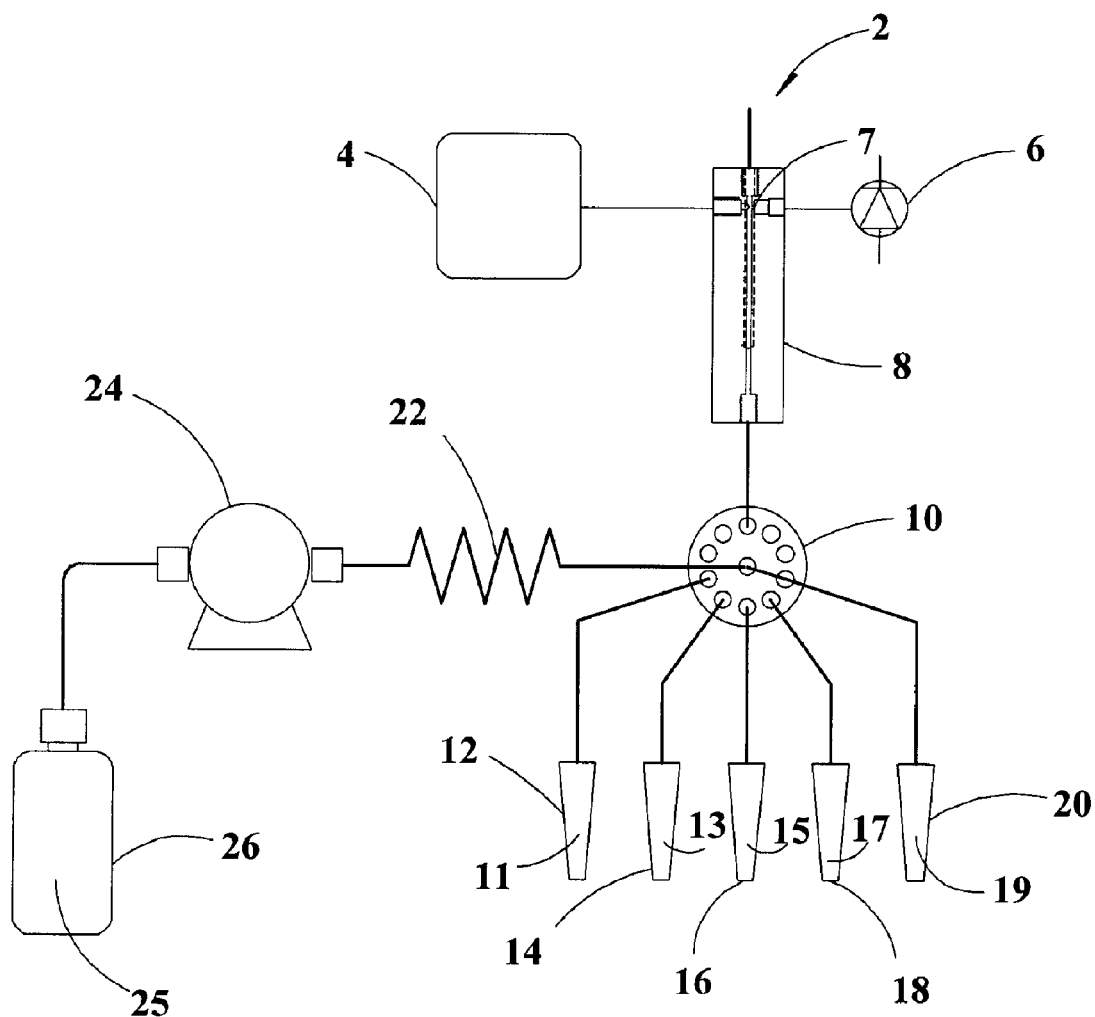
FIG. 1 is a schematic representation of a zone-fluidics analyzer, made in accordance with the principles of the present invention.

The present invention comprises the utilization of zone fluidics to determine both total and bound bilirubin in blood plasma. Three measurements are made for each sample of plasma, and the concentrations of total and bound bilirubin are derived from the resultant vector response.

More specifically, reference is made to FIG. 1, in which is shown a zone-fluidics analyzer, made in accordance with the principles of the present invention, and generally designated by the numeral 2.

The carrier stream 25 in the zone fluidics instrument 2 is distilled water doped with about eighty microliters (μl) of a surfactant, Zonyl FSN®, a registered trademark of Dupont de Nemours Company, Wilmington, Del., per hundred milliliters (ml) of distilled water. There are three reagents used in this assay. The first reagent 13 is a phosphate buffer containing chloride. Preferably, the buffer comprises from about one-tenth to about three-tenths of a mole of phosphate per liter (l), and from about one hundred to about two hundred micromoles (μmols) of chloride per l. Most preferably, the buffer contains approximately two-tenths of a mole of phosphate and approximately one-hundred-fifty μmols of chloride per l. The second reagent 15 is the same buffer containing hydrogen peroxide and D-glucose. Preferably, the second reagent 15 comprises from about one hundred to about onehundred-fifty μmols of hydrogen peroxide per l, and from about three hundred to about five hundred milligrams (mg) of D-glucose per deciliter (dl). Most preferably, the second reagent 15 comprises approximately one-hundred-twenty-five μmols of hydrogen peroxide per l, and approximately four hundred mg of D-glucose per dl. The third reagent 17 is the same buffer containing horseradish peroxidase and glucose oxidase. Preferably, the third reagent 17 comprises from about fifty to about one-hundred-fifty micrograms (μg) of horseradish peroxidase per milliliter (ml), with an activity of from about fourteen to about eighteen reciprocal minutes per μg; and from about forty to about eighty μg of glucose oxidase per ml, with an activity of from about two-hundred-ninety to about three hundred International Units (IU) per mg. Most preferably, the third reagent 17 comprises approximately one hundred μg of horseradish peroxidase per ml, with an activity of approximately 16.4 reciprocal minutes per μg; and approximately sixty μg of glucose oxidase per ml, with an activity of approximately two-hundred-ninety-six IU per mg. A total of twenty-four μl of plasma 11 sampleare used in the three measurements that are carried out. A wash solution 19 of sodium hydroxide of from about 0.05 to about 1.5 molar (M), preferably about 0.1 M, is plumbed to a selection valve 10, and is used to flush the system between measurements. A temperature-controlled heater 8 is used to keep the reaction temperature at approximately thirty-seven degrees Centigrade. All measurements are made at a two-fold sample dilution and a total volume (sample+reagents) of sixteen μl.

A sample of plasma 11 is disposed in a first reservoir 12, the first reagent 13 in a second reservoir 14, the second reagent 15 in a third reservoir 16, the third reagent 17 in a fourth reservoir 18, the sodium hydroxide wash solution 19 in a fifth reservoir 20, and the carrier 25 in a container 26.

The detector comprises a combination of a multiwave spectrometer 4 and a white-light-emitting diode 6.

Liquid portions of sample 11 and reagents 13, 15, 17 are withdrawn from the reservoirs 12, 14, 16, and 18 by means of the selection valve 10 and a pump 24, and are mixed in a holding coil 22.

The total bilirubin concentration (TBC) is measured by creating and mixing in the holding coil 22 the following zone stack: a liquid zone comprising four μl each of the first and second reagents 13 and 15, and eight μl of sample 11, sandwiched between two ten-microliter air zones. Using the selection valve 10 and the pump 24, the zones are heated to from about thirty to about forty degrees Centigrade by passage through the heater 8 via a flow cell 7. When mixing and reaction are complete, as judged by the consistency of the optical density (OD) at four-hundred-sixty nanometers (nm) as the reagent-sample zone moves through the flow cell 7 past the detector 4,6, the TBC is calculated from the OD using Beer's law. The μmol/l extinction coefficient Eat one-centimeter path length is 0.0485.

The $B_f$ is measured at two peroxidase concentrations, the first $B_f$ determination $B_f$ being made after combining four μl each of the second and third reagents 15 and 17 with eight μl of sample 11, and the second $B_{f-half}$ after combining four μl of the second reagent 15, and two μl each of the third and first reagents 17 and 13 with eight μl of sample 11. When the zone stack reaches the detector flow cell 7, flow is stopped so that the enzymatic decay reaction can be monitored. The $B_f$ at each peroxidase concentration can be calculated from the change in the OD at four-hundred-sixty nm. The peroxidase has previously been standardized by measuring its catalytic activity for the oxidation of bilirubin by peroxide in the absence of albumin. Standardization is performed by measuring the change in OD at four-hundred-forty nm, the maximum absorbance for bilirubin not bound to albumin, in three milliliters (ml) of one-tenth molar (0.1 M) phosphate buffer containing hydrogen peroxide (one-hundred-twenty-five μmol/l), bilirubin (ca. three μmol/l) to which diluted stock peroxidase has been added. The rate constant k of the Arrows stock peroxidase diluted 1:24562.2 is −0.0166 (standard deviation 0.05) reciprocal seconds. $B_f$ (μmol/l) in a plasma sample is calculated from the change in absorbance A460 at 460 nm over t seconds (A460$_0$ at t=0 sec to A460$_t$ at t sec), ϵ(0.00245 l/μmol), and the ratio of the concentrations (dilutions) of stock peroxidase used in the reaction (D) and standardization (24562.2) as follows:

$$B_f(\mu mol/l)=[A460_0 \ln(A460_t/A460_0)D]/[24562.2\epsilon kt]$$

A critical condition of the peroxidase test is that the rate of bilirubin oxidation be extremely slow relative to the rate at which bilirubin dissociates from albumin to replace the reacting bilirubin; otherwise the steady-state bilirubin and therefore the apparent $B_f$ will be significantly less than the equilibrium (true) $B_{fe}$. This condition can be verified and, if necessary, corrected for by measuring $B_f$ at more than one peroxidase concentration. If dissociation of bilirubin from albumin is rate-limiting, the apparent $B_f$ will increase as the peroxidase concentration decreases. In the zone fluidics test, two peroxidase concentrations are used, differing by 50%. If $B_f$ is greater at the lower peroxidase concentration ($B_{f1}$) exceeds the $B_f$ at the higher peroxidase concentration ($B_{f2}$) by more than the error of the method (i.e. is more than 5% higher), both the measured $B_f$ values underestimate $B_{fe}$, which can be calculated from the two values as $$B_{fe}=0.5B_{f1}/(1-0.5B_{f1}/B_{f2})$$

The following data were obtained from newborn plasma using the zone fluidics instrument 2 and methods described above.

HRP=Horseradish Peroxidase

|  | TBC (mg/dl) | $B_f$ (μg/dl) Full HRP | $B_f$ (μg/dl) ½HRP | $B_f$ (μg/dl) Equilibrium |
|---|---|---|---|---|
|  | 8.16 | 4.79 | 5.83 | 7.45 |
|  | 8.20 | 4.90 | 6.27 | 8.70 |
|  | 8.28 | 4.77 | 6.43 | 9.86 |
|  | 8.24 | 4.45 | 6.34 | 11.02 |
|  | 8.35 | 4.89 | 6.68 | 10.54 |
| Average | 8.25 | 4.76 | 6.31 | 9.51 |
| SD | 0.073 | 0.183 | 0.310 | 1.446 |
| CV | 0.89% | 3.84% | 4.91% | 15.20% |

SD=Standard Deviation
Full HRP=128-fold dilution of stock peroxidase ($B_{f2}$)
½ HRP=256-fold dilution of stock peroxidase ($B_{f1}$)
CV=Coefficient of Variation The regression line for the zone fluidics instrument for TBC compared with the Arrows instrument is Y=1.09x−0.81, a nearly 1:1 correlation (n=47, paired t-test, average difference 0.085, 95% Confidence Interval: −0.08 to 0.25, which is probably not significant). The correlation between the zone fluidics instrument and Arrows $B_f$ is Y=4.3x−0.8, $r^2$=0.85, where r, where r is the correlation coefficient; a significant regression, but the typical $B_f$ is four-fold greater at the two-fold sample dilution used by the zone fluidics instrument compared with the forty-two-fold dilution used by the Arrows device.

The attenuating effect of dilution on the effect of weak bilirubin binding competitors was tested by adding 500 μmol/l sulfisoxazole to an artificial serum consisting of defatted human albumin (3 g/dl) and bilirubin (molar ratio of sulfisoxazole to bilirubin approximately 1.1). Sulfisoxazole is an antibiotic known to compete with bilirubin for albumin-binding sites, and which, when given to newborns, has caused kernicterus. The mean $B_f$ measured by the Arrows instrument at a forty-two fold sample dilution was 1.34 µg/dl (SD 0.05, n=4) before and 1.71 µg/dl (SD 0.05, n=4) after sulfisoxazole, a 28% increase. The mean $B_f$ measured using the zone fluidics device 2 was 3.16 µg/dl (SD 0.04, n=4) before and 6.87 (SD 0.4, n=4) after sulfisoxazole, a 119% increase. Accurate measurement of the $B_f$ by the Arrows instrument is clearly compromised when bilirubin-binding competitors are present.

Zone fluidics, when used for measuring bilirubin in newborn plasma, uses small sample and reagent volumes, and significantly reduces dilution errors that occur in the Arrows method caused by inherent changes in bilirubin-binding with sample dilution, as well as the effects of weak bilirubin-binding competitors.

While certain embodiments and details have been described to illustrate the principles of the present invention, it will be apparent to those skilled in the art that many modifications are possible within the scope of the claimed invention.

We claim:

1. A method for determining total bilirubin in plasma, the method comprising the steps of:
    (a) disposing a sample of plasma in a first reservoir;
    (b) disposing a first reagent in a second reservoir;
    (c) disposing a second reagent in a third reservoir;
    (d) connecting the first, second, and third reservoirs to a selection valve;
    (e) using the selection valve to dispose a first air zone in a holding coil; (f) using the selection valve to dispose a liquid zone in the holding coil by withdrawing, under conditions of fluid flow, portions of the first and second reagents from the second and third reservoirs, respectively, and of the sample from the first reservoir, and mixing the portions of the first and second reagents and of the sample in the holding coil;
    (g) using the selection valve to dispose a second air zone in the holding coil, thereby disposing the liquid zone between the first and second air zones, and forming a zone stack comprising the first air zone, the liquid zone, and the second air zone;
    (h) passing the zone stack by a detector; and
    (i) using the detector to generate a signal indicative of concentration of total bilirubin in the sample.

2. The method of claim 1, wherein the first reagent is a phosphate buffer containing chloride, and the second reagent is the phosphate buffer containing hydrogen peroxide and D-glucose.

3. The method of claim 2, wherein the zones are heated to a temperature of from about thirty degrees to about forty degrees Centigrade before using the detector to generate a signal indicative of the concentration of bilirubin in the sample.

4. The method of claim 1, wherein the first reagent comprises a concentration of from about one-tenth to about three-tenths moles per liter phosphate buffer, and from about one hundred to about two hundred micromoles per liter of chloride; and the second reagent comprises a concentration of from about one-tenth to about three-tenths moles per liter phosphate buffer, from about one hundred to about one-hundred-fifty micromoles per liter hydrogen peroxide, and from about three hundred to about five hundred milligrams per deciliter D-glucose.

5. The method of claim 4, wherein the zones are heated to a temperature of from about thirty degrees to about forty degrees Centigrade before using the detector to generate a signal indicative of the concentration of bilirubin in the sample.

6. The method of claim 1, wherein the zones are heated to a temperature of from about thirty degrees to about forty degrees Centigrade before using the detector to generate a signal indicative of the concentration of bilibrubin in the sample.

7. A method for determining unbound bilirubin in plasma, the method comprising the steps of:
    (a) disposing a sample of plasma in a first reservoir;
    (b) disposing a first reagent in a second reservoir;
    (c) disposing a second reagent in a third reservoir;
    (d) disposing a third reagent in a fourth reservoir;
    (e) connecting the first, second, third, and fourth reservoirs to a selection valve;
    (f) using the selection valve to dispose a first air zone in a holding coil;
    (g) using the selection valve to dispose a first liquid zone in the holding coil by withdrawing, under conditions of fluid flow, portions of the second reagent, the third reagent, and the sample from the third, fourth, and first reservoirs, respectively, and mixing the portions of the second reagent, the third reagent, and the sample in the holding coil;
    (h) using the selection valve to dispose a second air zone in the holding coil, thereby disposing the first liquid zone between the first and second air zones, and forming a first zone stack comprising the first air zone, the first liquid zone, and the second air zone;
    (i) passing the first zone stack to a detector;
    (j) stopping fluid flow when the first zone stack reaches the detector;
    (k) observing change of signal from the detector over a period of time;
    (l) using the selection valve to dispose a third air zone in the holding coil;
    (m) using the selection valve to dispose a second liquid zone in the holding coil by withdrawing, under conditions of fluid flow, portions of the second reagent, the third reagent, the first reagent, and the sample from the third, fourth, second, and first reservoirs, respectively, and mixing the portions of the second reagent, the third reagent, the first reagent, and the sample in the holding coil;
    (n) using the selection valve to dispose a fourth air zone in the holding coil, thereby disposing the second liquid zone between the third and fourth air zones, and forming a second zone stack comprising the third air zone, the second liquid zone, and the fourth air zone;
    (O) passing the second zone stack to the detector;
    (p) stopping fluid flow when the second zone stack reaches the detector;
    (q) observing change of signal from the detector over a period of time; and
    (r) calculating concentration of unbound bilirubin from rates of change of detector response.

8. The method of claim 7, wherein the first reagent is a phosphate buffer containing chloride, the second reagent is the phosphate buffer containing hydrogen peroxide and D-glucose, and the third reagent is the phosphate buffer containing horseradish peroxidase and glucose oxidase.

9. The method of claim 8, wherein the zones are heated to a temperature of from about thirty to about forty degrees Centigrade before observing a change of signal from the detector over a period of time.

10. The method of claim 7, wherein the first reagent comprises a concentration of from about one-tenth to about three-tenths moles per liter phosphate buffer, and from about one hundred to about two hundred micromoles per liter chloride; the second reagent comprises a concentration of from about one-tenth to about three-tenths molers per liter phosphate buffer, from about one hundred to about one-hundred-fifty micromoles per liter hydrogen peroxide, and from about three hundred to about five hundred milligrams per deciliter D-glucose; and the third reagent comprises a concentration of from about fifty to about one-hundred-fifty micrograms of horseradish peroxidase, with an activity of from about fourteen to about eighteen reciprocal minutes, and from about forty to about eighty micrograms of glucose oxidase per milliliter, with an activity of from about two-hundred-ninety to about three hundred International Units per milligram.

11. The method of claim 10, wherein the zones are heated to a temperature of from about thirty to about forty degrees Centigrade before observing a change of signal from the detector over a period of time.

12. The method of claim 7, wherein the zones are heated to a temperature of from about thirty to about forty degrees Centigrade before observing a change of signal from the detector over a period of time.

* * * * *